US011751623B2

(12) United States Patent
Sernfält et al.

(10) Patent No.: US 11,751,623 B2
(45) Date of Patent: Sep. 12, 2023

(54) WELDING HELMET

(71) Applicant: 3M INNOVATIVE PROPERTIES COMPANY, St. Paul, MN (US)

(72) Inventors: Mats U. Sernfält, Leksand (SE); Björn Daniels, Vikarbyn (SE)

(73) Assignee: 3M Innovative Properties Company, St. Paul, MN (US)

( * ) Notice: Subject to any disclaimer, the term of this patent is extended or adjusted under 35 U.S.C. 154(b) by 61 days.

(21) Appl. No.: 16/644,047

(22) PCT Filed: Sep. 19, 2018

(86) PCT No.: PCT/IB2018/057230
§ 371 (c)(1),
(2) Date: Mar. 3, 2020

(87) PCT Pub. No.: WO2019/058287
PCT Pub. Date: Mar. 28, 2019

(65) Prior Publication Data
US 2020/0205507 A1 Jul. 2, 2020

(30) Foreign Application Priority Data
Sep. 22, 2017 (EP) .................................. 17192508

(51) Int. Cl.
*A42B 3/22* (2006.01)
*A61F 9/06* (2006.01)
*A61F 9/04* (2006.01)
(52) U.S. Cl.
CPC .............. *A42B 3/225* (2013.01); *A42B 3/222* (2013.01); *A61F 9/045* (2013.01); *A61F 9/06* (2013.01); *A61F 9/064* (2013.01)
(58) Field of Classification Search
CPC ............. A42B 3/225; A61F 9/06; A61F 9/064
(Continued)

(56) References Cited

U.S. PATENT DOCUMENTS 1,800,623 A * 4/1931 Greene ................... A61F 9/061
2/8.2
3,945,043 A * 3/1976 DeAngelis ............. A42B 3/223
2/8.1
(Continued)

FOREIGN PATENT DOCUMENTS

CN 207627482 U * 7/2018 ............. A42B 3/225
EP 2786669 A1 10/2014
(Continued)

OTHER PUBLICATIONS

Extended EP Search Report for EP17192508.4, PCT/IB2018/057230, dated Mar. 9, 2018, 2 pgs.
(Continued)

*Primary Examiner* — Khoa D Huynh
*Assistant Examiner* — Grace Huang
(74) *Attorney, Agent, or Firm* — Gregg H. Rosenblatt

(57) ABSTRACT

A welding helmet (1) has a protective shield (2) and a first swivel mechanism (10) that pivotally connects the protective shield with a head suspension system (6) for swiveling about a swivel axis. The first swivel mechanism enables the protective shield and the head suspension system to be swiveled between a lowered position, in which the protective shield covers a wearer's face, and an upraised position, in which the protective shield uncovers the wearer's face. The first swivel mechanism (10) has a recess (16*a*) and a retainer (17*a*) for engaging with the recess. The retainer and the recess are arranged to engage with each other in the upraised position, and to remain disengaged in the lowered position and between the lowered position and the upraised position.

15 Claims, 6 Drawing Sheets

(58) Field of Classification Search
USPC .......................................... 2/8.2, 8.5, 6.4, 6.5
See application file for complete search history.

(56) References Cited

U.S. PATENT DOCUMENTS

| | | | |
|---|---|---|---|
| 4,464,800 A | 8/1984 | Edwards | |
| 5,301,372 A | 4/1994 | Matoba | |
| 6,282,726 B1 * | 9/2001 | Noyerie | A42B 3/226 |
| | | | 2/424 |
| 6,298,498 B1 | 10/2001 | Burns | |
| 6,438,763 B2 * | 8/2002 | Guay | A42B 3/226 |
| | | | 2/424 |
| 6,795,979 B2 * | 9/2004 | Fournier | A42B 3/10 |
| | | | 2/424 |
| 7,594,278 B2 * | 9/2009 | Huh | A61F 9/025 |
| | | | 2/9 |
| 8,056,152 B2 * | 11/2011 | Brace | A42B 3/225 |
| | | | 2/424 |
| 8,166,577 B2 * | 5/2012 | Lee | A42B 3/222 |
| | | | 2/424 |
| 8,291,513 B2 * | 10/2012 | Prinkey | A42B 3/22 |
| | | | 2/15 |
| 8,336,114 B1 | 12/2012 | Lee | |
| 8,381,312 B2 * | 2/2013 | Seo | A61F 9/064 |
| | | | 2/8.4 |
| 10,667,952 B2 * | 6/2020 | Magnusson | A61F 9/067 |
| 2007/0124851 A1 | 6/2007 | Pyo | |
| 2007/0159684 A1 * | 7/2007 | Roy | A61F 9/064 |
| | | | 359/361 |
| 2010/0005558 A1 | 1/2010 | Lee | |
| 2013/0212785 A1 | 8/2013 | Ratti et al. | |
| 2015/0359679 A1 | 12/2015 | Sommers et al. | |
| 2016/0331059 A1 * | 11/2016 | Basson | A42B 3/085 |
| 2020/0068979 A1 * | 3/2020 | Muske | A42B 3/20 |

FOREIGN PATENT DOCUMENTS

| | | | | |
|---|---|---|---|---|
| EP | 3241533 A1 * | 11/2017 | | A61F 9/06 |
| GB | 690284 A * | 4/1953 | | A61F 9/06 |
| GB | 2153003 | 8/1985 | | |
| JP | 07216622 | 8/1995 | | |
| JP | 07216622 A * | 8/1995 | | A42B 3/225 |
| TW | M485719 U | 9/2014 | | |

OTHER PUBLICATIONS

International Search Report for PCT International Application No. PCT/IB2018/057230, dated Dec. 13, 2018, 5 pages.
Search Report for CN Application No. 201880060540.5, dated Jan. 24, 2022, 3 pp.

* cited by examiner

WELDING HELMET

FIELD OF THE INVENTION

The invention relates to a welding helmet that has a protective shield that can be swiveled between a lowered position and an upraised position in which the protective shield is retained.

BACKGROUND ART

Welding helmets are typically used in the mechanical and industrial art to protect welders from harmful irradiation emitted from the welding arc and from splashes, sparks and particles that may be ejected from welding area. Welding helmets typically can be suspended on the head of a wearer, so that the wearer has both hands available for welding and handling of workpieces.

Some welding helmets are furnished with an automatic darkening filter. An automatic darkening filter commonly has a switchable filter that automatically changes from a light-state to a dark-state in response to incident light generated by the welding arc. Thus, upon ignition of the welding arc the switchable filter automatically changes to the dark-state and protects the welder's eyes from the irradiation of the welding arc. Once the welding is interrupted or ended the switchable filter automatically changes to the light-state so that the user can see through the filter at normal light conditions.

Accordingly there are welding helmets that stay in position on a wearer's head independent from the actual welding actions, for example during locating of the electrode toward the workpiece to be welded or during handling. There are however situations in which it may be desired to put off the welding helmet, for example for communicating or during handling of workpieces or welding equipment.

There are welding helmets that have a protective shield that is used in a lowered position and which can be lifted toward an upraised position so that the protective shield uncovers the wearer's face. Typically such welding helmets can be fixed in the upraised position by tightening a screw, or the protective shield may be only movable at relatively high forces to avoid self-returning of the protective shield toward the lowered position.

Although existing welding helmet provide for a variety of advantages there is still a need for a welding helmet that provides for easy handling and which helps maximizing the safety in the area of welding.

SUMMARY OF THE INVENTION

The invention relates to a welding helmet that comprises a protective shield and a first swivel mechanism. The first swivel mechanism pivotally connects the protective shield with a head suspension system. In particular the first swivel mechanism pivotally connects the protective shield with the head suspension system for swiveling about a swivel axis. The first swivel mechanism enables the protective shield to be swiveled relative to the head suspension system between a lowered position, in which the protective shield covers a wearer's face, and an upraised position, in which the protective shield uncovers the wearer's face. The first swivel mechanism comprises a recess and a retainer for engaging with the recess. The retainer and the recess are arranged to engage with each other in the upraised position, and to remain disengaged in the lowered position and between the lowered position and the upraised position.

The invention is advantageous in that it provides for a welding helmet that allows for swiveling the protective shield out of a wearer's field of vision relatively quickly, and for retaining the protective shield in the upraised position. Further the retention of the protective shield in the upraised position can be established without applying an additional torque on the torque required for swiveling of the protective shield in other positions between the lowered and the upraised position. Thus the risk of pushing off the helmet from a wearer's head during swiveling the protective shield toward the upraised position is minimized. Further, due to the possibility of swiveling the protective shield to an upraised position in which the protective shield is retained the safety can be maximized. This is because the advantages of the welding helmet of the invention help minimizing minimize any desire of the wearer to put off the welding helmet completely.

In one embodiment the first swivel mechanism provides for an angular swivel range over which the protective shield can be swiveled at a uniform first swiveling torque (or a generally uniform first swiveling torque). This angular swivel range preferably ranges over all positions between the upraised position and the lowered position and preferably includes the lowered position but not the upraised position.

In a further embodiment the welding helmet provides for a total opening angle of the protective shield relative to the head suspension system about the swivel axis. The total opening angle is greater than the angular swivel range and includes the upraised position. Preferably the total opening angle is greater than 70 degrees, for example 71 degrees.

Preferably any swiveling over the transition from a position between the lowered and the upraised position into the upraised position is enabled at the first swiveling torque. This means that preferably no additional torque is needed to swivel the protective shield from a position between the lowered and the upraised position into the upraised position.

In one embodiment in the upraised position the retainer and the recess impede any swiveling of the protective shield and the head suspension system toward the lowered position. The retainer and the recess preferably impede the swiveling by virtue of their engagement. In particular in the upraised position the retainer protrudes into the recess in a dimension that is transverse to a dimension along which the swiveling is enabled. Thus the swiveling is only enabled in consequence of the retainer and the recess disengage.

In one embodiment the first swivel mechanism comprises a support surface within which the recess is arranged. The retainer is preferably resiliently urged toward the support surface and/or toward the recess. In particular, the retainer is preferably resiliently urged onto the support surface outside the upraised position. Thus the retainer is arranged to snap in the recess upon reaching the upraised position. The retainer may be formed by a bulge or raised structure, like a raised pad, button, ball or roll.

In one embodiment in the upraised position the first swivel mechanism enables a swiveling of the protective shield and the head suspension system relative to each other toward the lowered position (only) via overcoming a break loose torque. Preferably outside the upraised position any swiveling torque (in particular the first swiveling torque) required to swivel the protective shield and the head suspension system relative to each other is lower than the break loose torque. Preferably the break loose torque is caused by a force that is required to urge the retainer out of the recess. Such force includes for example the force at which the retainer is urged into the recess and friction forces. Once the break loose torque is reached the retainer preferably unsnaps so that swiveling out of the upraised position is enabled.

In an embodiment the welding helmet further comprises a first adjustment wheel. The first adjustment wheel is provided for adjusting a force at which the retainer is urged toward the support surface and thereby for adjusting the break loose torque. The welding helmet further preferably comprises a resilient washer. The resilient washer is preferably put under pretension by the first adjustment wheel to provide the force at which the retainer is urged toward the support surface. The resilient washer may be a spring washer or an elastic ring, for example.

In a preferred embodiment the support surface is rotationally symmetric. In particular the support surface may be planar. Other shapes are possible. For example the support surface may be conical, toric, cylindrical or a combination thereof. The support surface may extend at least over a part of a circumference around the swivel axis. The support surface may further extend circumferentially around the swivel axis.

In an embodiment the first swivel mechanism comprises a first swivel part that comprises the recess, and a second swivel part that comprises the retainer. The second swivel part may be formed by the protective shield. Further, the retainer may be formed by the protective shield. Preferably the first swivel part is attachable or attached with the head suspension system. The first swivel part may further by formed by the head suspension system. Preferably the first and second swivel part are arranged rotatable to each other about the swivel axis.

In one embodiment the first swivel mechanism comprises a plurality of recesses. Further, the first swivel mechanism may comprise a corresponding plurality of retainers. The recesses and the retainers may be uniformly distributed around the swivel axis. For example the first swivel mechanism may comprise three recesses and three retainers that are arranged by 120 degrees offset from each other around the swivel axis. Further the retainers and the recesses are arranged at a radius from the swivel axis and may be sized so that they can mate when they are angularly aligned with each other about the swivel axis.

In one embodiment the welding helmet comprises the head suspension system. The head suspension system comprises at least a headband.

In a further embodiment the welding helmet further comprises a second swivel mechanism. Preferably the first and second swivel mechanisms are arranged at opposite sides of the welding helmet. Preferably the second swivel mechanism additionally pivotally connects the protective shield with the head suspension system for swiveling about the swivel axis. The second swivel mechanism is preferably configured for adding a friction torque to any torque required for swiveling of the protective shield and the head suspension system relative to each other. The second swivel mechanism may be particularly configured for adding a friction torque to any friction torque provided by the first swivel mechanism. Such a friction torque may for example be adjusted to compensate for a torque that is generated in consequence of the protective shield's own weight. Thus, the friction torque may provide for a smooth swiveling outside the upraised position or may prevent any self-acting swiveling of the protective shield. The second swivel mechanism may comprise a second adjustment wheel for adjusting the friction torque. The second swivel mechanism thus allows for adjusting the friction torque independent of any adjustment of the break loose torque provided by the first swivel mechanism. This means that for example the break loose torque is not lowered or increased when the friction force is changed.

In a further embodiment the protective shield comprises a clear visor. The welding helmet preferably has a welding visor that is arranged pivotally relative to the clear visor for pivoting between a welding position in which the welding visor covers the clear visor and a non-welding position in which the welding visor uncovers the clear visor. The pivot range between the welding visor and the protective shield is preferably greater than 50 degrees, in particular 51 degrees.

In one embodiment the welding visor comprises an automatic darkening filter. The automatic darkening filter is preferably based on two liquid crystal cells. The liquid crystal cells are electrically switchable between a light-state and a dark-state. The two liquid crystal cells are preferably arranged optically in sequence. Each liquid crystal cell comprises two transparent substrates with a liquid crystal layer arranged between. Each substrate is provided with an alignment layer that is in contact with the liquid crystal layer. The alignment layers provide for a default uniform alignment of the liquid crystals. Further, the two liquid crystal cells preferably comprise three polarizers, one of which being arranged between the two liquid crystal cells and the other two being arranged on outer sides. The outer side polarizers may be arranged with their light polarizing orientation in the same or substantially the same direction, whereas the inner polarizer may be oriented with its light polarizing orientation 90 degrees or substantially 90 degrees relative to the outer polarizers.

In the light-state the transmittance of the automatic darkening filter may be within a range of about 1% to about 20%, in more particular within a range of about 5% to about 10%, whereas in the dark-state the transmittance of the automatic darkening filter may be within a range of about 0.0005% to about 0.1%.

In one embodiment the welding visor comprises a permanent optical filter (instead of an automatic darkening filter). Such an optical filter may have a permanent transmittance within a range of about 0.0005% to about 0.1%.

In a further embodiment the welding helmet has a sensor for detecting light, as for example light emitted from the welding arc. The sensor and the automatic darkening filter are functionally interconnected so that light above a predetermined light intensity detected by the sensor causes the automatic darkening filter to switch to the dark-state and the absence or non-detection of light above the predetermined light intensity causes the automatic darkening filter to switch to the light-state.

DETAILED DESCRIPTION OF THE INVENTION

Figure 1:
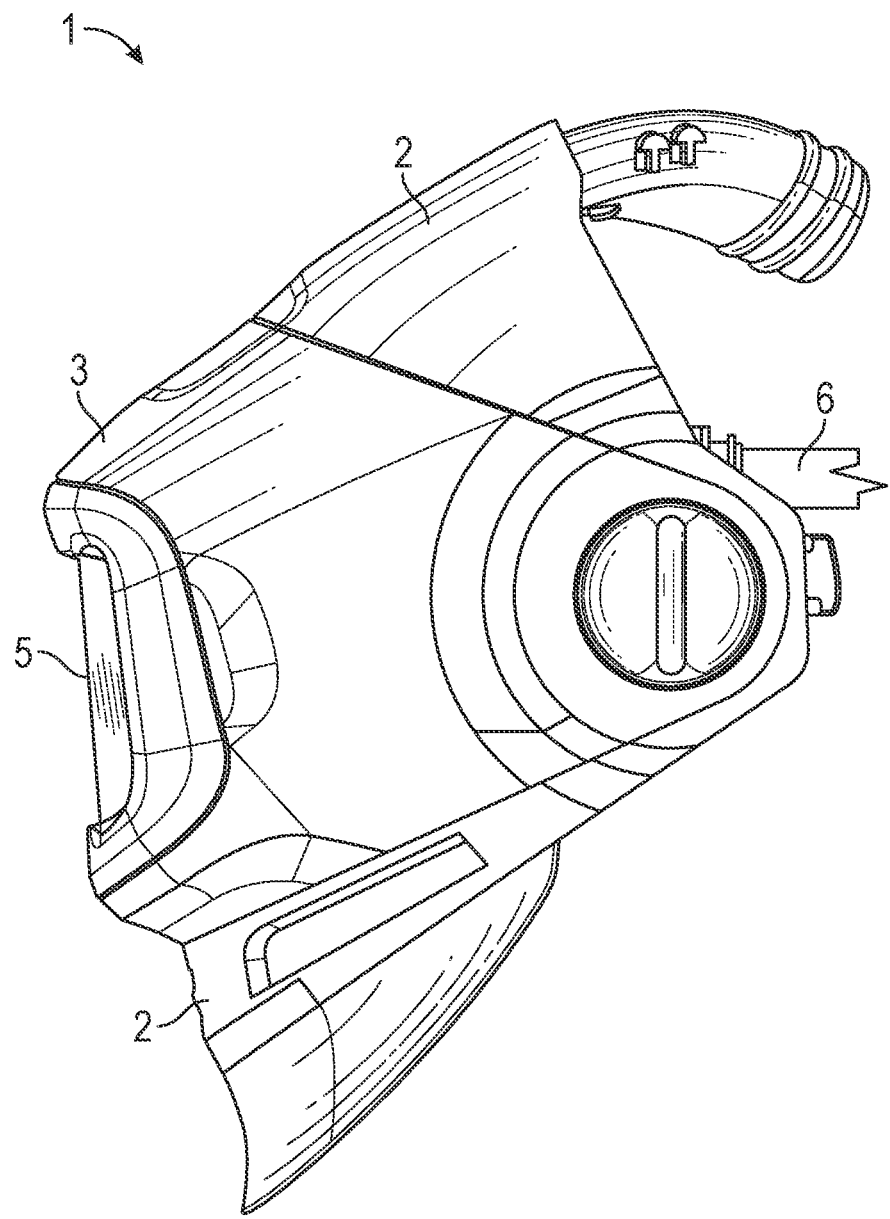
FIG. 1 is a side view of a welding helmet according to an embodiment of the invention.

FIG. 1 shows a welding helmet 1 according to the invention. The welding helmet 1 has a protective shield 2 which is illustrated in a lowered position that corresponds to a position in which the protective shield 2 covers a wearer's face. The welding helmet 1 further has a head suspension system 6 for supporting the welding helmet 1 on a wearer's head. The welding helmet 1 further has a welding visor 3. The welding visor 3 is configured to filter those portions of light of a welding arc that would be harmful for a wearer of the welding helmet 1 observing the welding arc through the welding visor 3.

The welding visor 3 comprises an automatic darkening filter 5. The automatic darkening filter 5 allows a welder to safely observe the welding arc during welding. In the example the automatic darkening filter 5 is based on two liquid crystal cells. The liquid crystal cells are electrically switchable between a light-state and a dark-state. When switched in the dark-state, the automatic darkening filter 5 blocks a significant amount of light from being transmitted therethrough. This enables a user to observe a welding arc by seeing through the automatic darkening filter 5 without risking to be exposed to harmful light radiation from the welding arc. In the light-state the automatic darkening filter 5 permits a significant amount of light to be transmitted therethrough. Thus, the automatic darkening filter 5 in the light-state allows the user to see under ambient light conditions (in the absence of the welding arc). The two (or more) liquid crystal cells are arranged optically in sequence. This provides for multiplying the darkening effect (in particular in the dark-state) and thus a sufficient eye protection from light radiation.

The welding visor 3 is illustrated in a welding position in which the welding visor 3 covers a see-through window (indicated as number 4 in FIG. 2) provided in the protective shield 2. The welding visor 3 is however pivotable between the welding position (shown in FIG. 1) and a non-welding position (shown in FIG. 2).

Figure 2:
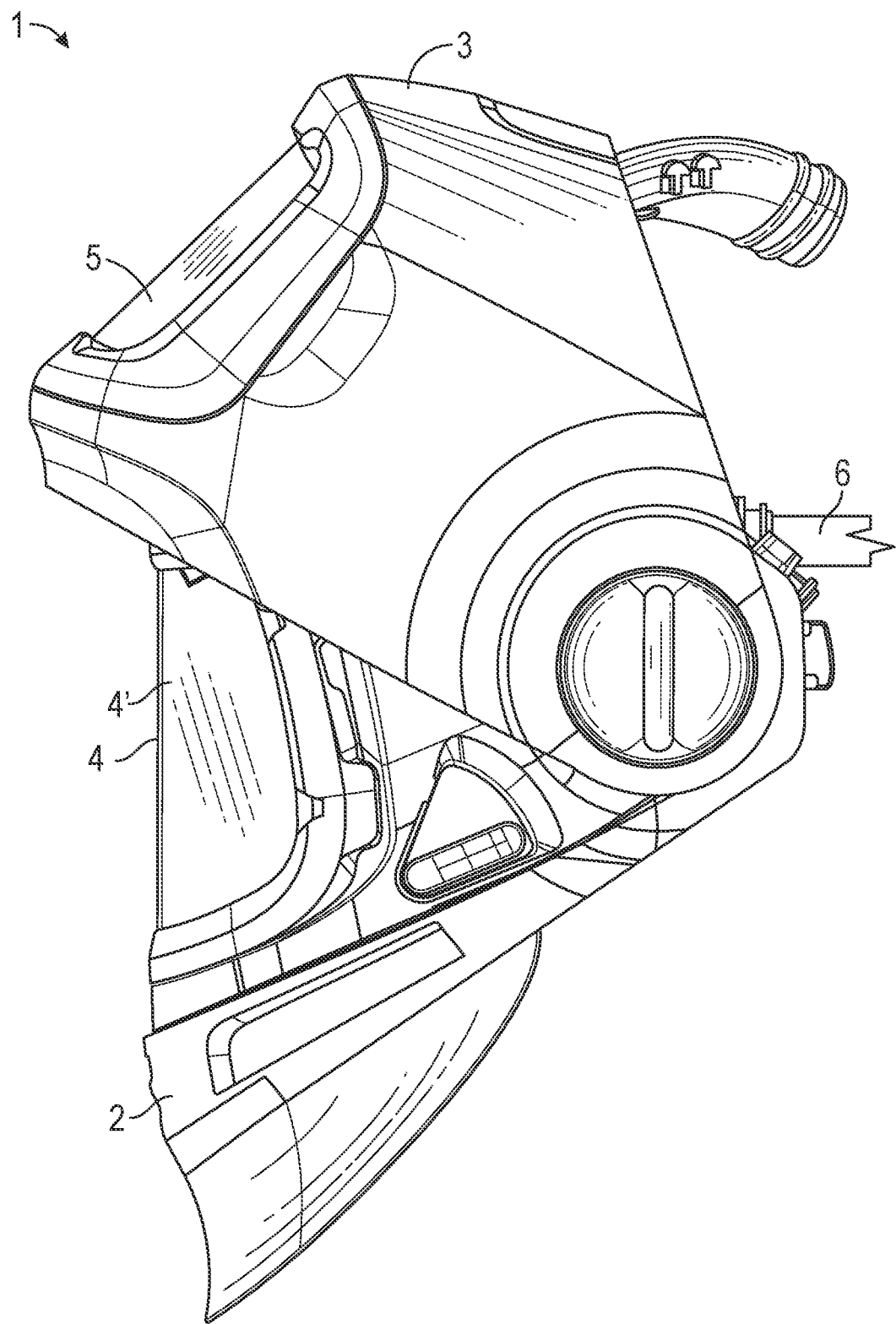
FIG. 2 is a further side view of the welding helmet according to an embodiment of the invention.

FIG. 2 shows the welding helmet 1 with the welding visor 3 in the non-welding position in which the welding visor uncovers the see-through window 4. The protective shield 2 is still in the lowered position. The protective shield 2 has a clear visor 4' that closes the see-through window 4 in the protective shield 2. Thus, a wearer's face is protected by the protective shield 2 and the clear visor 4' for example from particles ejected from a workplace the wearer faces toward. Although the clear visor 4' does not provide a sufficient protection against harmful light emitted from a welding arc, the clear visor 4' allows the wearer of the welding helmet 1 to see through the clear visor 4' at ambient light conditions. Therefore, in the lowered position of the protective shield 2 with the welding visor 3 being in the non-welding position the welding helmet 1 may for example be used for protecting a wearer during grinding or similar works.

Figure 3:
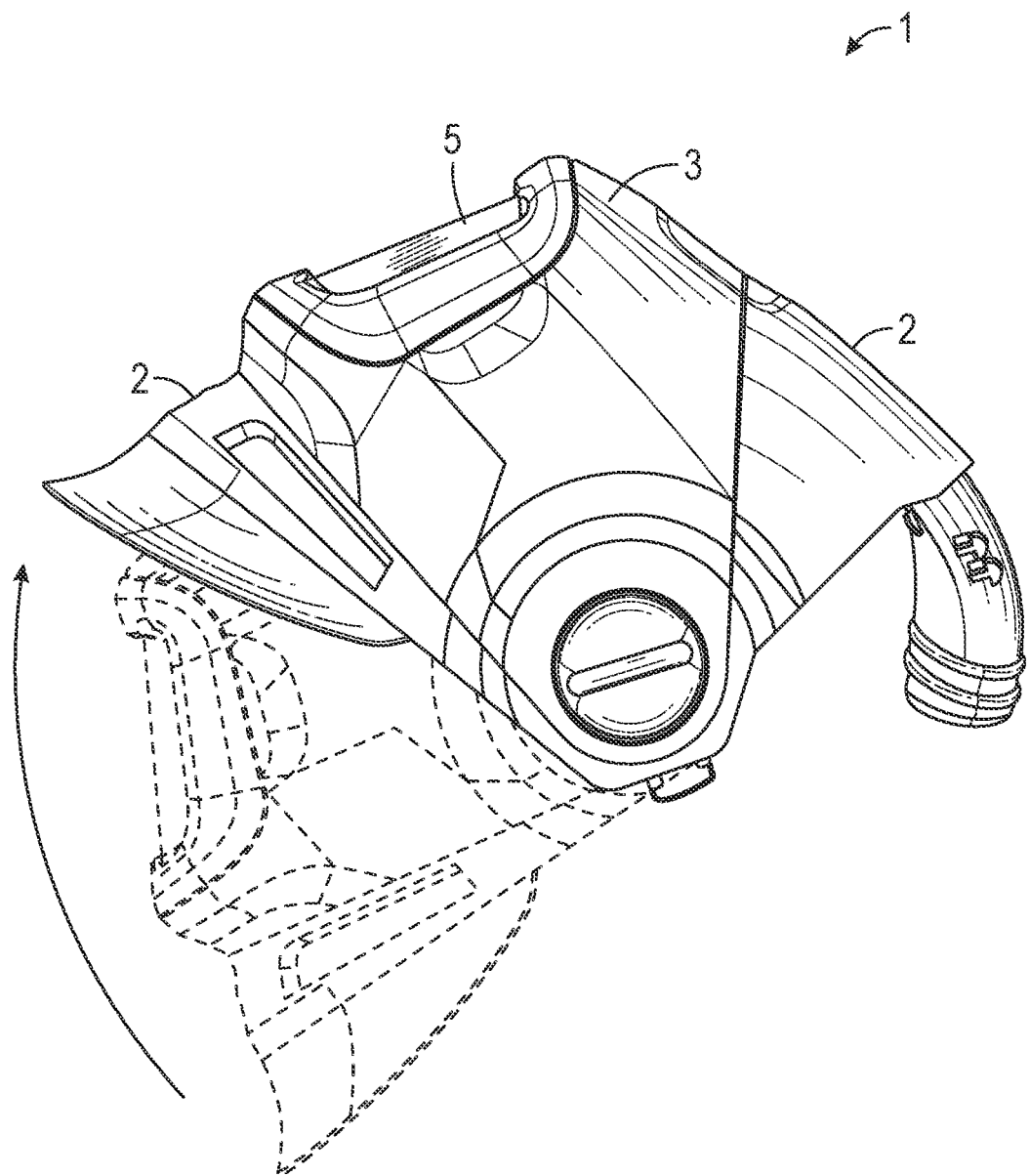
FIG. 3 is a side view of the welding helmet illustrating an upraised position of the protective shield relative to the lowered position according to an embodiment of the invention.

As illustrated in FIG. 3 the protective shield 2 of the welding helmet 1 further can be lifted or swiveled to an upraised position to fully uncover a wearer's face. The swiveling of the protective shield 2 is provided relative to the head suspension system 6. Accordingly, the welding helmet 1 is configured such that the welding shield 2 can be swiveled on a wearer's head while the head suspension system 6 remains in place. The swiveling of the protective shield 2 relative to the head suspension system 6 is independent from the pivoting of the welding visor 3 relative to the protective shield 2. Thus, the position of the welding visor 3 relative to the protective shield 2 is not changed by changing the position of the protective shield 2 relative to the head suspension system 6. This allows a wearer of the welding helmet 1 to temporarily lift the protective shield 2 away from his or her face toward the upraised position and to continue using the welding helmet 1 with the protective shield 2 in the lowered position after, without changing the position of the welding visor 3.

Figure 4:
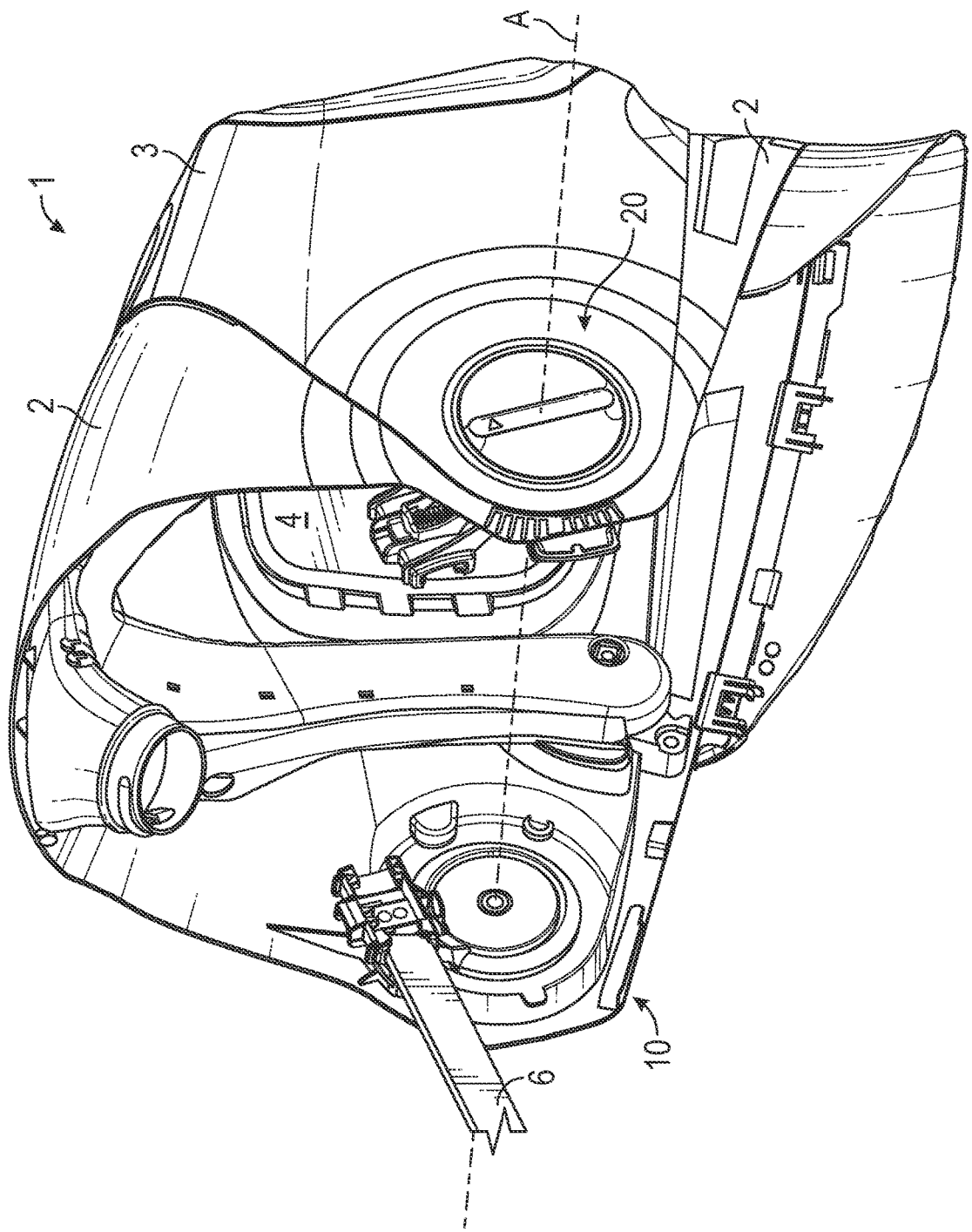
FIG. 4 is a perspective rear view of the welding helmet according to an embodiment of the invention.

The swiveling function of the protective shield 2 relative to the head suspension system is provided by a first swivel mechanism 10 as well as by a second swivel mechanism 20 as shown in FIG. 4. The first and second swivel mechanism 10, 20 each pivotally connect the protective shield with the head suspension system 6 for swiveling about a swivel axis A. The first and second swivel mechanism 10, 20 are arranged on opposite sides on the protective shield. Therefore, the first and second swivel mechanism 10, 20 in combination additionally guide the swiveling parallel to a plane perpendicular about the swivel axis A. The first and second swivel mechanism 10, 20 further provide different functions. In particular, the first swivel mechanism 10 exclusively provides a parking position for the protective shield 2 in the upraised position, whereas the second swivel mechanism 20 exclusively provides for an adjustable friction at which the protective shield 2 during swiveling between the upraised position and the lowered position. Further, the first swivel mechanism 10 allows for adjusting a torque required to leave the parking position. In other words the first swivel mechanism 10 allows for adjusting a retention at which the protective shield 2 is retained in the parking position independently of the adjustment of the friction torque required for swiveling between the lower and the upraised position. The second swivel mechanism 20 allows for adding a torque that is required to swivel the protective shield 2 and the head suspension system relative to each other. The second swivel mechanism 20 therefore can be used to add a torque that compensates for the weight of the protective shield 2. Therefore via the second swivel mechanism 20 the welding helmet 1 can be adjusted to avoid that the protective shield 2 rapidly returns to the lowered position due to its own weight in any position between the upraised and the lowered position.

The first swivel mechanism 10 in particular enables the protective shield 2 and the head suspension system 6 to be swiveled between the lowered position and an upraised position.

Figure 5:
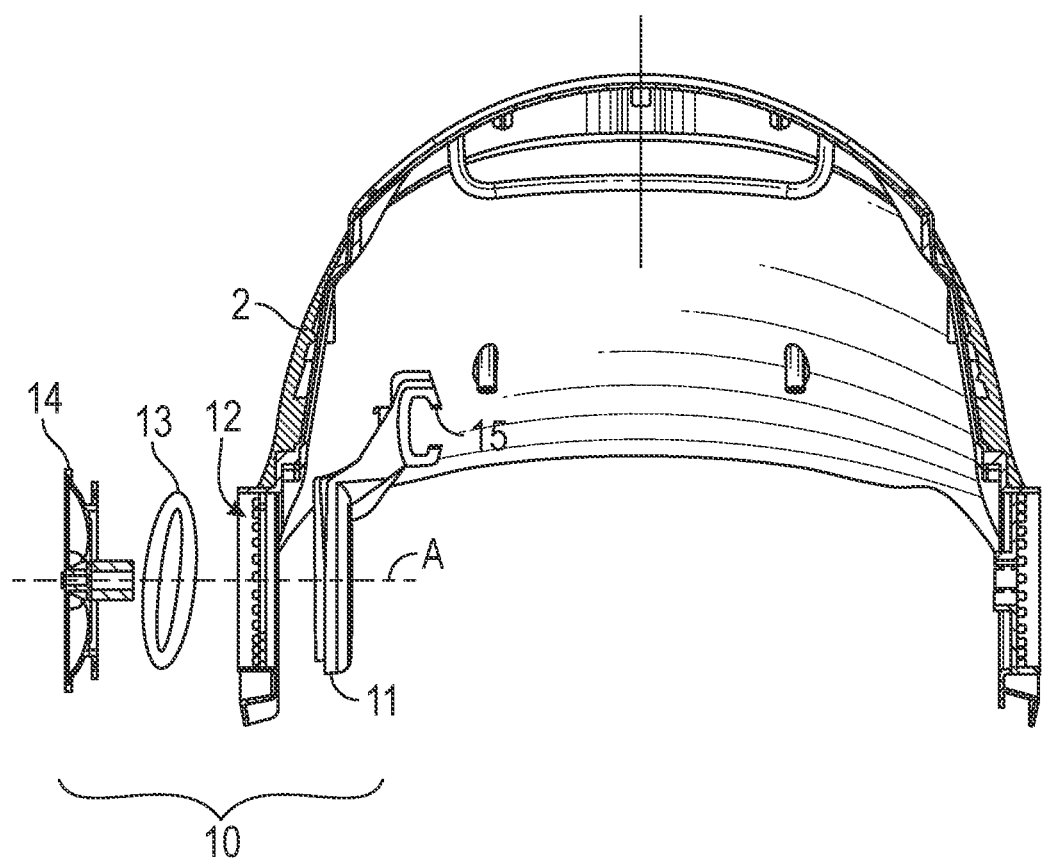
FIG. 5 is a partial exploded view of the welding helmet according to an embodiment of the invention.

FIG. 5 shows the first swivel mechanism 10 in more detail. The first swivel mechanism 10 comprises a first swivel part 11, a second swivel part 12, a resilient washer 13 and a first adjustment wheel 14. The second swivel part 12 (in the example) is formed by a portion of the protective shield 2. The first swivel part 11 has an interface extension arm 15 to attach the head band (not illustrated in this view). The first and second swivel part 11, 12 are rotatable to each other when the first swivel mechanism 10 is assembled. The first adjustment wheel 14 can be screwed into the first swivel part 11 with the resilient washer 13 arranged between the first adjustment wheel 14 and the second swivel part 12. Thereby the first adjustment wheel 14 extends through the resilient washer 13 and the second swivel part 12 into the first swivel part 11. The adjustment of the first swivel mechanism 10 can be performed by tightening or loosening the screw connection between the first adjustment wheel 14 and the first swivel part 11. This causes the first and second swivel part 11, 12 to be urged more or less tightly, respectively, onto another. The force at which the first and second swivel part 11, 12 are urged onto another is maintained by a pretension generated within the resilient washer 13. The resilient washer 13 further allows a certain resilient movement of the first and second swivel part 11, 12 in an axial dimension of the swivel axis A.

Figure 6:
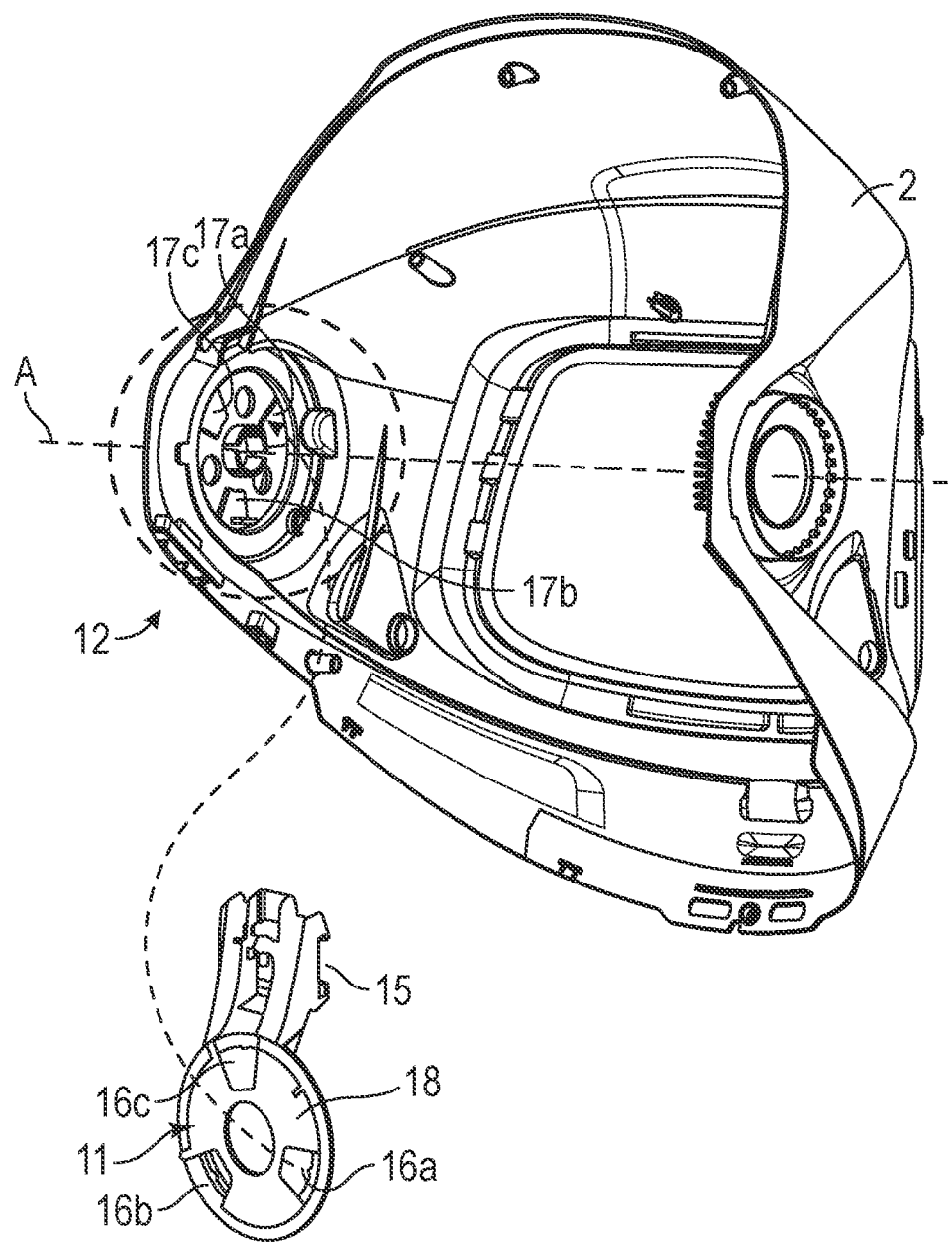
FIG. 6 is a partial view of the protective shield and a first swivel part according to an embodiment of the invention.

As shown in FIG. 6 the first swivel part 11 comprises a recess 16a and the second swivel part 12 comprises a retainer 17a. Although illustrated taken apart from each other the first swivel part 11 and the second swivel part 12 can be mated as indicated by the arrow. When mated, the first and second swivel part can rotate relative to each other. The rotation of the first and second swivel part 11, 12 relative to each other enables the protective shield 2 and the first swivel part 11 to rotate relative to each other. Because the first swivel part 11 is typically fixed with the head suspension system (not shown in this view), thus the rotation of the first and second swivel part 11, 12 relative to each other also enables the protective shield 2 and the head suspension system to swivel relative to each other. In the upraised position of the protective shield 2 the retainer 17a and the recess 16a engage with each other. The engagement between the retainer 17a and the recess 16a hinders the protective shield and the head suspension system to be swiveled relative to each other toward the lowered position. However, the protective shield and the head suspension system can be swiveled toward the lowered position upon overcoming a break loose torque applied in the upraised position. Exceeding the break loose torque causes the retainer 17a and the recess 16a to disengage or unsnap from each other so that the retainer 17a can slide on support surface 18 until the lowered position is reached. During the swiveling from the upraised position to the lowered position the retainer 17a slides on support surface 18 which provides for a uniform (or substantially uniform) swivel torque. Also during the swiveling in the opposite direction, from the lowered position to the upraised position the retainer 17a slides on support surface 18 which again provides for a uniform (or substantially uniform) swivel torque. In more particular during the swiveling from the lowered position to the upraised position no additional torque is needed for the engagement of the retainer 17a and the recess 16a. This is minimizes the risk that a wearer in swiveling the protective shield 2 into the upraised position causes the welding helmet to inadvertently push off the head. In that regard it is noted that there is a lower risk of pushing off the welding helmet from the wearer's head in swiveling the protective shield out of the upraised position toward the lowered position. This is due to the different leverages that the head suspension system provides with respect to the forces occurring from the swiveling in the different directions.

Any swiveling torque required to swivel the protective shield and the head suspension system relative to each other is lower than the break loose torque. Therefore the protective shield 2 can be safely retained in the upraised position while the protective shield 2 can be easily swiveled down to the lowered position.

In the example the first swivel part 11 has three recesses 16a, 16b, 16c and the second swivel part 12 has three retainers 17a, 17b, 17c. The recesses 16a-16c are uniformly distributed over a circumference around the swivel axis A, and the retainers 17a-17c are uniformly distributed over a circumference around the swivel axis A. Therefore the recesses 16a-16c and the retainers 17a-17c are angularly offset by 120 degrees. This enables a swivel angle of the protective shield 2 and the head suspension system of at least 70 degrees, which has been found appropriate in the use of welding helmets.

The invention claimed is:

1. A welding helmet configured to be worn by a wearer, comprising:

a protective shield configured to fully cover the wearer's face when placed in a first position and fully uncover the wearer's face when placed in a second position;

a head suspension system coupled to the protective shield and configured to support the protective shield on the wearer's head; and a first swivel mechanism fixed to the head suspension system, pivotally connecting the protective shield with the head suspension system, and configured to swivel the protective shield relative to the head suspension system about a swivel axis from the first position to the second position, wherein the first swivel mechanism comprises one or more recesses and one or more retainers, wherein each of the one or more recesses is configured to engage a retainer of the one or more retainers, wherein in the second position at least one retainer is engaged in at least one recess, wherein in the first position none of the one or more retainers are engaged in any of the one or more recesses, and wherein all of the one or more retainers remain disengaged from all of the one or more recesses when the protective shield is swiveled from the first position to the second position wherein the first swivel mechanism further includes an interface extension arm to attach the first swivel mechanism to the head suspension system.

2. The welding helmet of claim 1, wherein in the second position the one or more retainers engaged in the one or more recesses is configured to impede any swiveling of the protective shield and the head suspension system toward the first position.

3. The welding helmet of claim 1, wherein the first swivel mechanism comprises a support surface within which the one or more recesses are arranged, wherein the one or more retainers are configured to be resiliently urged onto the support surface so as to snap in the one or more recesses upon reaching the second position.

4. The welding helmet of claim 3, wherein in the second position the first swivel mechanism enables a swiveling of the protective shield relative to the head suspension system toward the first position via overcoming a break loose torque, and wherein, when the protective shield is in a position other than the second position, any swiveling torque required to swivel the protective shield relative to the head suspension system is lower than the break loose torque.

5. The welding helmet of claim 4, further comprising a first adjustment wheel for adjusting a force at which the one or more retainers are urged toward the support surface and thereby for adjusting the break loose torque.

6. The welding helmet of claim 5, further comprising a resilient washer that is put under pretension by the first adjustment wheel to provide the force at which the one or more retainers are urged toward the support surface.

7. The welding helmet of claim 5, further comprising a second swivel mechanism that additionally pivotally connects the protective shield with the head suspension system for swiveling about the swivel axis, wherein the second swivel mechanism is configured for adding a friction torque to any torque required for swiveling of the protective shield relative to the head suspension system.

8. The welding helmet of claim 7, wherein the second swivel mechanism comprises a second adjustment wheel for adjusting the friction torque.

9. The welding helmet of claim 3, wherein the support surface is rotationally symmetric, wherein a shape of the support surface is selected from the group consisting of planar, conical, toric and cylindrical, and wherein the support surface extends at least over a part of a circumference around the swivel axis.

10. The welding helmet of claim 1, wherein the first swivel mechanism comprises a first swivel part that comprises the one or more recesses, and wherein the one or more retainers are disposed on a second swivel part formed by the protective shield, and wherein the first swivel part is attachable to the head suspension system.

11. The welding helmet of claim 1, wherein the first swivel mechanism comprises three recesses and three retainers that are arranged by 120 degrees offset from each other around the swivel axis.

12. The welding helmet of claim 1, wherein the head suspension system comprises a head band.

13. The welding helmet of claim 1, wherein the protective shield comprises a clear visor, and wherein the welding helmet has a welding visor that is arranged pivotally relative to the clear visor for pivoting between a welding position in which the welding visor covers the clear visor and a non-welding position in which the welding visor uncovers the clear visor.

14. The welding helmet of claim 13, wherein the welding visor has an automatic darkening filter.

15. The welding helmet of claim 1, wherein a swivel angle about the swivel axis between the first position and the second position is at least 70 degrees.

\* \* \* \* \*

UNITED STATES PATENT AND TRADEMARK OFFICE
CERTIFICATE OF CORRECTION

Page 1 of 1

PATENT NO. : 11,751,623 B2
APPLICATION NO. : 16/644047
DATED : September 12, 2023
INVENTOR(S) : Mats Sernfält It is certified that error appears in the above-identified patent and that said Letters Patent is hereby corrected as shown below:

In the Claims

<u>Column 8</u>
Line 20, In Claim 1, insert --,-- after "the second position".

Signed and Sealed this
Twenty-fifth Day of June, 2024

Katherine Kelly Vidal
*Director of the United States Patent and Trademark Office*